United States Patent [19]

Hubele et al.

[11] Patent Number: 5,538,979
[45] Date of Patent: Jul. 23, 1996

[54] MICROBICIDES

[75] Inventors: Adolf Hubele, Magden, Switzerland; Ronald Zeun, Neuenburg, Germany

[73] Assignee: Ciba-Geigy Corporation, Tarrytown, N.Y.

[21] Appl. No.: 437,730

[22] Filed: May 9, 1995

Related U.S. Application Data

[62] Division of Ser. No. 300,499, Sep. 2, 1994, Pat. No. 5,447,935, which is a division of Ser. No. 166,780, Dec. 14, 1993, Pat. No. 5,373,013, which is a division of Ser. No. 16,365, Feb. 11, 1993, abandoned.

[30] Foreign Application Priority Data

Feb. 13, 1992 [CH] Switzerland .................. 427/92

[51] Int. Cl.⁶ .................. A01N 43/54; A01N 43/64
[52] U.S. Cl. .................. 514/275; 514/383
[58] Field of Search .................. 514/275, 383

[56] References Cited

U.S. PATENT DOCUMENTS

| | | | |
|---|---|---|---|
| 3,952,002 | 4/1976 | Kramer et al. | 260/308 |
| 4,510,136 | 4/1985 | Moberg | 514/63 |
| 4,532,341 | 7/1985 | Holmwood et al. | 549/559 |
| 4,626,595 | 12/1986 | Holmwood et al. | 549/559 |
| 4,652,580 | 3/1987 | Janssen et al. | 514/383 |
| 4,664,696 | 5/1987 | Schaub | 71/92 |
| 4,723,984 | 2/1988 | Holmwood et al. | 71/76 |
| 4,789,672 | 12/1988 | Holmwood et al. | 514/184 |
| 4,871,390 | 10/1989 | Holmwood et al. | 71/92 |
| 4,897,107 | 1/1990 | Holmwood et al. | 71/92 |
| 4,904,298 | 2/1990 | Holmwood et al. | 71/92 |
| 4,906,652 | 3/1990 | Karbach et al. | 514/383 |
| 4,911,746 | 3/1990 | Holmwood et al. | 71/92 |
| 4,992,438 | 2/1991 | Ito et al. | 514/275 |

FOREIGN PATENT DOCUMENTS

| | | |
|---|---|---|
| 0015756 | 9/1980 | European Pat. Off. . |
| 0251775 | 1/1988 | European Pat. Off. . |
| 0151404 | 6/1980 | Germany . |
| 1522657 | 8/1978 | United Kingdom . |
| 2098607 | 11/1982 | United Kingdom . |
| 2112287 | 7/1983 | United Kingdom . |
| 2119653 | 11/1983 | United Kingdom . |

OTHER PUBLICATIONS

Worthing et al, "The Pesticide Manual"; 9th ed. (1991) pp. 833–834.

Worthing et al, "The Pesticide Manual"; 9th ed. (1991) p. 277.

*Primary Examiner*—Allen J. Robinson
*Attorney, Agent, or Firm*—Edward McC. Roberts

[57] ABSTRACT

Mixtures of certain triazole fungicides (component I) and 4,6-dimethyl-N-phenyl-2-pyrimidinamine (component II) achieve synergistically enhanced activity against fungus infestation. Components I and II can also be applied to plant crops individually, one immediately after the other.

5 Claims, No Drawings

MICROBICIDES

This application is a division of U.S. application Ser. No. 08/300,499, filed Sep. 2, 1994, now Pat. No. 5,447,935, issued Sep. 5, 1995, which is a division of U.S. application Ser. No. 08/166,780, filed Dec. 14, 1993, now U.S. Pat. No. 5,373,013, which issued Dec. 13, 1994, which is a division of U.S. application Ser. No. 08/016,365, filed Feb. 11, 1993, now abandoned.

MICROBICIDES

The present invention relates to fungicidal two-component mixtures having synergistically enhanced action and to methods for the application of such mixtures in crop protection.

Component I is an ergosterol-biosynthesis inhibitor of the triazole series, or a salt or metal complex thereof, selected from A) 1-[2-(2,4-dichlorophenyl)-4-propyl-1,3-dioxolan-2-ylmethyl]-1H- 1,2,4-triazole, trade name propiconazol, (reference: GB 1 522 657);

B) 1-{2-[2-chloro-4-(4-chlorophenoxy)phenyl]-4-methyl-1, 3-dioxolan-2 -ylmethyl}-1H- 1,2,4-triazole, trade name difenoconazol, (reference: GB 2 098 607);

C) α-[2-(4-chlorophenyl)ethyl]-α-(1,1-dimethylethyl)-1H-1,2,4-triazol-1-ethanol, trade name tebuconazol, (reference: EP-A-40 345);

D) 1-(4-chlorophenoxy)-3,3-dimethyl-1-(1,2,4-triazol-1-yl)-butan-2-ol, trade name triadimenol, (reference: DE-OS 23 24 010);

E) 1-[3-(2-chlorophenyl)-2-(4-fluorophenyl)oxiran-2-ylmethyl]-1H-1,2,4-triazole, code name BAS-480-F, (reference EP-A-196 038);

F) α-(4-chlorophenyl)-α-(1-cyclopropylethyl)-1H-1,2,4-triazol-1-ethanol, trade name cyproconazol (reference: U.S. Pat. No. 4,664,696);

G) 4-(4-chlorophenyl)-2-phenyl-2-(1,2,4-triazol-1-ylmethyl)butyronitrile, proposed trade name fenbuconazol (reference: EP-A-251 775);

H) α-(2-fluorophenyl)-α-(4-fluorophenyl)-1H-1,2,4-triazol-1-ethanol, trade name flutriafol (reference: EP-A-15 756);

J) α-butyl-α-(2,4-dichlorophenyl)-1H-1,2,4-triazol-1-ethanol, trade name hexaconazol (reference: GB-2 119 653); and K) 1-{[bis(4-fluorophenyl)methylsilyl]methyl}-1H-1,2,4-triazole, trade name flusilazol (reference: U.S. Pat. No. 4,510,136).

Component II is the 2-anilinopyrimidine of the formula

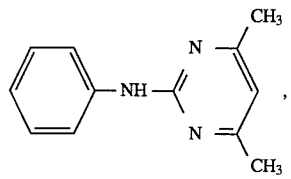

4,6-dimethyl-N-phenyl-2-pyrimidinamine, proposed trade name pyrimethanil, or a salt or metal complex thereof (reference: DD 151 404).

Of the acids that can be used in the preparation of salts of formula I or II there may be mentioned:
hydrohalic acid, such as hydrofluoric acid, hydrochloric acid, hydrobromic acid or hydriodic acid, and sulfuric acid, phosphoric acid, nitric acid and organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1,2-naphthalenedisulfonic acid.

The term "salts" also includes metal complexes of the two basic components I and II. It is possible for only one of the components or, alternatively, for both components independently to be in the form of a complex, as desired. It is also possible to produce metal complexes that combine the two active ingredients I and II with one another to form a mixed complex.

Metal complexes comprise the basic organic molecule and an inorganic or organic metal salt, for example the halides, nitrates, sulfates, phosphates, acetates, trifluoroacetates, trichloroacetates, propionates, tartrates, sulfonates, salicylates, benzoates etc. of the elements of the second main group, such as calcium and magnesium, and of the third and fourth main groups, such as aluminium, tin or lead, and also of the first to eighth sub-groups, such as chromium, manganese, iron, cobalt, nickel, copper, zinc, etc. The sub-group elements of the 4th period are preferred. The metals may be present in any of their various valencies. The metal complexes may be mononuclear or polynuclear, that is to say, they may contain one or more organic molecules as ligands, as, for example, in the case of the above-mentioned mixed complexes of triazole component I and anilinopyrimidine II.

The triazole components I may be in stereoisomeric form or in the form of racemates. While components IC and IG to IJ can form two stereoisomers, four stereoisomers are possible for each of the other components IA (propiconazol), IB (difenoconazol), ID (triadimenol), IE (BAS-480-F) and IF (cyproconazol). The various stereoisomeric forms of the compounds may have different fungicidal actions. For example, in the case of propiconazol, the two cis-isomers are preferred, that is to say, those enantiomers in which the triazolylmethyl group and the propyl group are on the same side of the dioxolane ring. In the case of BAS-480-F, the two Z(=cis)-isomers are preferred.

In practice, the active ingredients I and II can advantageously be used in the form of free bases and in the form of racemates, to which there may also be added other agrochemical active substances, such as insecticides, acaricides, nematicides, herbicides, growth-regulators and fertilisers, but especially other microbicides.

In recent years so-called ergosterol-biosynthesis inhibitors have been introduced onto the market to a greater extent, that is to say, compositions of which the fungicidal action is based on preventing the biosynthesis of the ergosterol occurring in the cell membrane of fungi. Fungicides that contain a 1H-1,2,4-triazole radical in the molecule generally act as 14-C demethylation inhibitors (=DMI) during this process. The use over many years of compositions based on triazoles has, however, in some cases already led to the development of fungal strains that have demonstrably reduced sensitivity.

It has surprisingly now been found that mixtures of any triazole fungicides, and especially those of components I, and the anilinopyrimidine II, exhibit in their fungicidal action not only additive action but also distinct synergistically enhanced action, even in the case of fungus isolates that have acquired reduced sensitivity to triazole fungicides.

The present invention accordingly constitutes a very considerable enrichment of the art.

In addition to coveting the two-component mixture, the present invention relates also to a method of controlling fungi, which comprises treating a site that has been infested with fungi or is in danger of being so infested, in any sequence or simultaneously, with a) one of the components I or a (metal) salt thereof and with b) the active ingredient of formula II or a (metal) salt thereof, it also being possible for the choice of salts to be such that the two active ingredients are bonded to one acid radical or, in the case of a metal complex, to one central metal cation.

Favourable ratios of the two active ingredients are I:II= 7:1 to 1:30, preferably I:II=4:1 to 1:10. In many cases, mixtures in which the ratio of the pure active substances I:II=1:2 to 1:10, for example 1:3, 1:5, or 1:8, are advantageous.

The active ingredient mixtures I+II according to the invention possess very advantageous curative, preventive and systemic fungicidal properties for the protection of cultivated plants. With the present active ingredient mixtures, it is possible to inhibit or destroy the microorganisms occurring in plants or in parts of plants (fruit, blossoms, leaves, stems, tubers, roots) in different crops of useful plants, while at the same time the parts of plants which grow later are also protected from attack by such microorganisms. This applies especially also to microorganisms that have developed reduced sensitivity to fungicides of the triazole class.

The active ingredient mixtures are effective against the phytopathogenic fungi belonging to the following classes: Ascomycetes (for example Venturia, Podosphaera, Erysiphe, Monilinia, Uncinula); Basidiomycetes (for example the genera Hemileia, Rhizoctonia, Puccinia); Fungi imperfecti (for example Botrytis, Helminthosporium, Rhynchosporium, Fusarium, Septoria, Cercospora, Alternaria, Pyricularia and especially *Pseudocercosporella herpotrichoides*). The active ingredient mixtures have systemic action. They can also be used as dressing agents for protecting seeds (fruit, tubers, grains) and plant cuttings against fungus infections as well as against phytopathogenic fungi occurring in the soil. The active ingredient mixtures according to the invention are distinguished by the fact that they are especially well tolerated by plants and are environmentally friendly.

Target crops for the areas of indication disclosed herein are, within the scope of this invention, for example, the following plant species: cereals: (wheat, barley, rye, oats, rice, sorghum and related crops); beet: (sugar beet and fodder beet); pomes, drupes and soft fruit: (apples, pears, plums, peaches, almonds, cherries, strawberries, raspberries and blackberries); leguminous plants: (beans, lentils, peas, soybeans); oil plants: (rape, mustard, poppy, olives, sunflowers, coconut, castor oil plants, cocoa beans, groundnuts); cucumber plants: (cucumber, marrows, melons); fibre plants: (cotton, flax, hemp, jute); citrus fruit: (oranges, lemons, grapefruit, mandarins); vegetables: (spinach, lettuce, asparagus, cabbages, carrots, onions, tomatoes, potatoes, paprika); lauraceae: (avocado, cinnamon, camphor) or plants such as maize, tobacco, nuts, coffee, sugar cane, tea, vines, hops, bananas and natural rubber plants, as well as ornamentals (flowers, shrubs, deciduous trees and conifers). This list does not constitute a limitation.

The active ingredient mixtures of formulae I and II are normally applied in the form of compositions. The active ingredients of formula I and the active ingredient of formula II can be applied to the crop area or plant to be treated simultaneously or, alternatively, in succession on the same day, if desired together with further carriers, surfactants or other application-promoting additives customarily employed in formulation technology.

Suitable carriers and additives can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying an active ingredient mixture that comprises at least one of each of those active ingredients I and II is application to the parts of plants above the ground, especially the leaves (foliar application). The number of applications and the rate of application depend on the biological and climatic living conditions of the pathogen. However, the compounds can also penetrate the plant through the roots via the soil (systemic action) if the locus of the plant is impregnated with a liquid formulation, or if the compounds are applied in solid form to the soil, e.g. in granular form (soil application). The compounds of formulae I and II can also be applied to seeds (coating) either by impregnating the seeds in succession with a liquid formulation of a compound or by coating them with an already combined moist or dry formulation. Furthermore, in special cases, other types of application to plants are possible, e.g. the selective treatment of the buds or the infructescence.

The compounds of the combination are used in unmodified form or preferably together with the adjuvants conventionally employed in formulation technology, and are therefore formulated in known manner, e.g. into emulsifiable concentrates, coatable pastes, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application of the active ingredient mixture are generally from 150 g to 3 kg a.i./ha, especially from 200 g to 2 kg a.i./ha, especially preferably from 400 g to 1.5 kg a.i./ha.

The formulations are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Depending on the nature of the compounds of formulae I and II to be formulated, suitable surface-active compounds are nonionic, cationic and/or anionic surfactants having good emulsifying, dispersing and wetting properties. The term "surfactants" will also be understood as comprising mixtures of surfactants.

The surfactants customarily employed in formulation technology appear, inter alia, in the following publications: "McCutcheon's Detergents and Emulsifiers Annual" MC Publishing Corp., Glen Rock, N.J. 1988.

M. and J. Ash, "Encyclopedia of Surfactants", Vol. I–III, Chemical Publishing Co., New York, 1980–1981.

Especially advantageous, application-promoting additives are also natural or synthetic phospholipids from the series of the cephalins and lecithins, e.g. phosphatidylethanolamine, phosphatidylserine, phosphatidylglycerol and lysolecithin.

The agrochemical compositions generally comprise 0.1 to 99%, especially 0.1 to 95%, of compounds of formulae I and II, 99.9 to 1%, especially 99.9 to 5%, of a solid or liquid adjuvant and 0 to 25%, especially 0.1 to 25%, of a surfactant.

Whereas commercial products will preferably be formulated as concentrates, the end user will normally employ dilute formulations.

The present invention relates also to such (agro)chemical compositions.

The following Examples serve to illustrate the invention, the term "active ingredient" denoting a mixture of compound I and compound II in a specific ratio.

| Wettable powders | a) | b) | c) |
|---|---|---|---|
| active ingredient [I:II = 1:3(a), 1:5(b), 1.8(c)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| active ingredient (I:II = 2:5) | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in crop protection, can be obtained from this concentrate by dilution with water.

| Dusts | a) | b) | c) |
|---|---|---|---|
| active ingredient [I:II = 1:5 (a); 5:7 (b) and 1:2 (c)] | 5% | 6% | 4% |
| talcum | 95% | — | — |
| kaolin | — | 94% | — |
| mineral filler | — | — | 96% |

Ready-for-use dusts are obtained by mixing the active ingredient with the carrier and grinding the mixture in a suitable mill. Such powders can also be used as a dry dressing for seed.

| Extruder granules | |
|---|---|
| active ingredient (I:II = 2:3) | 15% |
| sodium lignosulfonate | 2% |
| carboxymethylcellulose | 1% |
| kaolin | 82% |

The active ingredient is mixed and ground with the adjuvants, and the mixture is subsequently moistened with water. The mixture is extruded and then dried in a stream of air.

| Coated granules | |
|---|---|
| active ingredient (I:II = 2:5) | 8% |
| polyethylene glycol (mol. wt. 200) | 3% |
| kaolin | 89% |

(mol. wt. = molecular weight)

The finely ground active ingredient is uniformly applied, in a mixer, to the kaolin moistened with polyethylene glycol. Non-dusty coated granules are obtained in this manner.

| Suspension concentrate | |
|---|---|
| active ingredient (I:II = 2:7) | 36% |
| propylene glycol | 10% |
| nonylphenol polyethylene glycol ether (15 mol of ethylene oxide) | 10% |
| sodium lignosulfonate | 10% |
| carboxymethylcellulose | 1% |
| silicone oil (in the form of a 75% aqueous emulsion) | 1% |
| water | 32% |

The finely ground active ingredient is intimately mixed with the adjuvants, giving a suspension concentrate from which suspensions of any desired dilution can be obtained by dilution with water. Using such dilutions it is possible to treat living plants and also plant propagation material by spraying, watering or impregnation and to protect them from attack by microorganisms.

BIOLOGICAL EXAMPLES

A synergistic effect always exists in the case of fungicides when the fungicidal action of the active ingredient combination is greater than the sum of the action of the active ingredients applied individually.

The expected action E for a given combination of active ingredients, for example two fungicides, obeys the so-called COLBY formula and can be calculated as follows (COLBY, L. R. "Calculating synergistic and antagonistic responses of herbicide combination". Weeds 15, pages 20–22.2) (LIMPEL et at., 1062 "Weed control by . . . certain combinations". Proc. NEWCL, Vol. 16, pp. 48–53): (g a.i./ha= gram active ingredient per hectare)

$X$=% action by fungicide I at $p$ g a.i./ha
$Y$=% action by fungicide H at $q$ g a.i./ha
$E$=the expected action of fungicides I+II at a rate of application of $p+q$ g a.i./ha (additive action),
thus, according to Colby: $E = X + Y - (X \cdot Y)/100$ If the action actually observed (0) is greater than the expected action, then the action of the combination is super-additive, that is to say, a synergistic effect exists.

ACTION AGAINST "POWDERY MILDEW" ON WINTER WHEAT

METHOD

In a greenhouse, approximately 20 plants of the winter wheat variety "Bernina" are grown in pots 16 cm in diameter at 20° C. and 60% relative humidity for 12 hours during the daytime and at 16° C. and 80% relative humidity during the night. When side-shoots start to form (EC 21), the plants are inoculated with an isolate of *Erysiphe graminis* f.sp. tritici that exhibits a reduced sensitivity to DMI fungicides.

3 days after the inoculation, the individual active ingredient or the fungicidal mixture is applied in the form of an aqueous suspension using a spray bar under field conditions at a rate of application of water of 500 l/ha. 4 days and 11 days after application the change in the infestation on the leaf surface present at the time of inoculation is determined (evaluation of primary infestation). 3 replicates are carried out for each test.

At various ratios of one of the components IA to IK and component II, a synergistically enhanced fungicidal action occurs.

Such enhancement of action is achieved not only against powdery mildew species but also against rust and scab diseases, stem-break, leaf blotch (for example Septoria or species of net blotch), grey mould rot and other pathogens.

Preferred ratios (in amounts by weight) are:

| | |
|---|---|
| IA:II = 5:1 to 1:30 | IF:II = 5:1 to 1:20 |
| IB:II = 3:1 to 1:11 | IG:II = 3:1 to 1:12 |
| IC:II = 3:1 to 1:8 | IH:II = 3:1 to 1:15 |
| ID:II = 7:1 to 1:12 | IJ:II = 5:1 to 1:24 |
| IE:II = 4:1 to 1:30 | IK:II = 2:1 to 1:14. |

What is claimed is:

1. A fungicidal, two-component composition containing a synergistically effective amount of a mixture of an ergosterol-biosynthesis inhibitor of the triazole series as component I and a 2-anilinopyrimidine derivative as component II, wherein the ratio of component I to component II is in the range of about 10:1 to 1:10, and wherein component I is difenoconazole or a salt or metal complex thereof; and component II is 4,6-dimethyl-N-phenyl- 2-pyrimidinamine or a salt or metal complex thereof, together with an inert carrier.

2. A composition according to claim 1, wherein the ratio by weight of I:II=4:1 to 1:10.

3. A composition according to claim 2, wherein the ratio by weight of I:II=1:2 to 1:10.

4. A method of controlling fungi or of preventing fungus infestation, wherein a part of the plant, that has been infested with fungi or is in danger of being so infested or the locus of the plant's growth is treated in any sequence or simultaneously with a synergistically effective amount of component I and component II according to claim 1.

5. A method according to claim 4, wherein the seed is treated.

* * * * *